United States Patent [19]
Hoffmann et al.

[11] 3,957,977
[45] May 18, 1976

[54] O-ALKYL-O-[3-METHYL-1,2,4-TRIAZOLO-(2,3,B)-THIAZOL(6)-YL](THIONO)-PHOSPHORIC (PHOSPHONIC) ACID ESTERS

[75] Inventors: Hellmut Hoffmann, Wuppertal; Ingeborg Hammann, Cologne; Wolfgang Behrenz, Overath-Steinenbruck; Wilhelm Stendel, Wuppertal, all of Germany

[73] Assignee: Bayer Aktiengesellschaft, Leverkusen, Germany

[22] Filed: Dec. 9, 1974

[21] Appl. No.: 531,025

[30] Foreign Application Priority Data
Dec. 10, 1973 Germany............... 2361451

[52] U.S. Cl..................... 424/200; 260/306.7 R; 260/306.7 E; 260/308 C
[51] Int. Cl.²........................ C07D 513/04
[58] Field of Search............ 260/306.7 E; 424/200

[56] References Cited
UNITED STATES PATENTS
3,682,943   8/1972   Hoffmann et al........... 260/306.7 E Primary Examiner—Raymond V. Rush
Attorney, Agent, or Firm—Burgess, Dinklage & Sprung

[57] ABSTRACT

O-Alkyl-O-[3-methyl-1,2,4-triazolo-(2,3,b)-thiazol(6)-yl]-(thiono)-phosphoric (phosphonic) acid esters of the formula

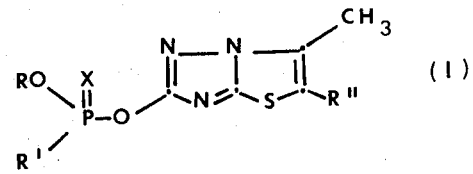

in which
R is alkyl with 1 to 6 carbon atoms,
R' is alkyl with 1 to 4 carbon atoms, alkoxy with 1 to 6 carbon atoms or phenyl,
R" is alkyl with 1 to 3 carbon atoms or alkylmercapto with 1 to 3 carbon atoms, and
X is oxygen or sulfur, which possess insecticidal and acaricidal properties.

12 Claims, No Drawings

O-ALKYL-O-[3-METHYL-1,2,4-TRIAZOLO-(2,3,b)-THIAZOL(6)-YL](THIONO)-PHOSPHORIC (PHOSPHONIC) ACID ESTERS

The present invention relates to and has for its objects the provision of particular new O-alkyl-O-[3-methyl-1,2,4-triazolo-(2,3,b)-thiazol(6)-yl]-(thiono)-phosphoric (phosphonic) acid esters, i.e. O,O-dialkyl-O-[2-alkyl- or -alkylmercapto- 3-methyl-1,2,4-triazole-(2,3,b)-thiazol(6)-yl]-phosphoric acid esters, their thiono and/or their alkanephosphonic acid ester counterparts, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,754,244 that pyrazolylthionophosphoric acid esters, for example O,O-diethyl-O-[3-methyl-pyrazol(5)yl]-thionophosphoric acid esters (Compound A), possess insecticidal and acaricidal activity.

The present invention provides triazolothiazolyl-(thiono)-phosphoric(phosphonic) acid esters of the general formula

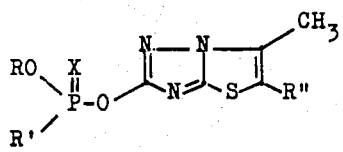

in which
R is alkyl with 1 to 6 carbon atoms,
R' is alkyl with 1 to 4 carbon atoms, alkoxy with 1 to 6 carbon atoms or phenyl,
R'' is alkyl with 1 to 3 carbon atoms or alkylmercapto with 1 to 3 carbon atoms, and
X is oxygen or sulfur.

Preferably, R is straight-chain or branched alkyl with 1 to 3 carbon atoms, R' is straight-chain or branched alkyl with 1 to 3 carbon atoms or alkoxy with 1 to 3 carbon atoms or phenyl, and R'' is methyl, ethyl, methylmercapto or ethylmercapto.

Surprisingly, the triazolothiazolyl-(thiono)-phosphoric(phosphonic) acid esters according to the invention have substantially better insecticidal and acaricidal activity than previously known compounds of analogous structure and of the same type of action. The compounds according to the invention thus represent a genuine enrichment of the art.

The invention also provides a process for the preparation of a triazolothiazolyl-(thiono)-phosphoric(phosphonic) acid ester of the formula (I) in which a (thiono)-phosphoric (phosphonic) acid ester halide of the general formula

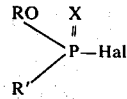

in which

R, R' and X have the above mentioned meanings, and
Hal is halogen, preferably chlorine, is reacted with a triazolothiazole derivative of the general formula

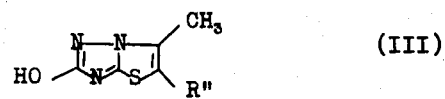

in which
R'' has the abovementioned meaning,
in the presence of an acid acceptor or in the form of a salt, preferably an alkali metal salt, alkaline earth metal salt or ammonium salt.

If, for example, 2-ethylmercapto-3-methyl-6-hydroxy-1,2,4-triazole-(2,3-b)-thiazole and O-ethyl-thionophenylphosphonic acid ester chloride are used as starting materials, the course of the reaction can be represented by the following formula scheme:

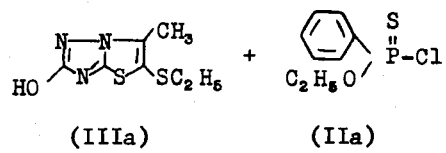

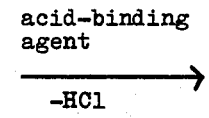

The (thiono)-phosphoric(phosphonic) acid ester halides (II) used as starting materials are already described in the literature and can be prepared by customary methods, e.g. U.S. Pat. No. 3,167,574 and German Published Specification DAS No. 1,067,017.

The following are specific examples thereof: O,O-dimethyl-, O,O-diethyl, O,O-di-n-propyl-, O,O-di-iso-propyl-, O-ethyl-O-n-propyl-, O-ethyl-O-iso-propyl- and O-n-propyl-O-methylphosphoric acid ester chloride and the corresponding thiono compounds and also O-methyl-, O-ethyl-, O-n-propyl- and O-iso-propyl-methane-, -ethane-, -propane- and -phenylphosphonic acid ester chloride and the corresponding thiono analogues.

The triazolothiazole derivatives (III) also required as starting materials are new, but they can be prepared, for example, by reacting thiosemicarbazide with pyrocarbonic acid ethyl ester to give an intermediate of the formula $$H_2N-CS-NH-NH-CO-OC_2H_5 \quad (IV)$$

then cyclizing the latter in the presence of alkali metal alcoholate and thereafter reacting the product, for example with 2-chlorobutanone-(3) or alkylmercapto-chloroacetone, and closing the thiazole ring, in the presence of a mineral acid, for example sulfuric acid, in accordance with the following formula scheme:

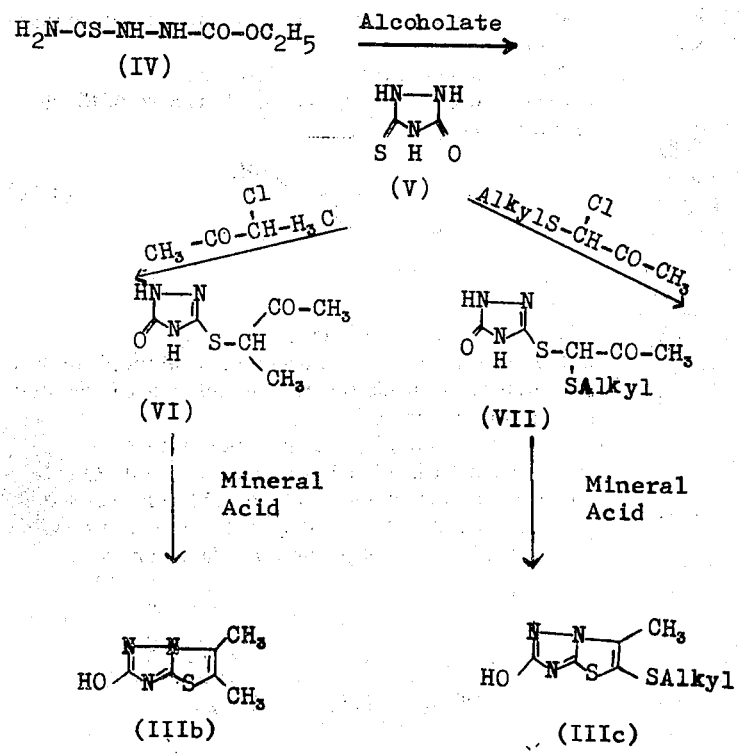

The following are specific examples of triazolothiazole derivatives (III): 2-methyl-, 2-ethyl-, 2-methylmercapto- and 2-ethylmercapto-3-methyl-6-hydroxy-1,2,4-triazolo(2,3-b)- thiazole.

The reaction according to the present invention is preferably carried out in the presence of a solvent which term includes a mere diluent. Practically all inert organic solvents can be used for this purpose. These include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate, methylate and ethylate and potassium carbonate, methylate and ethylate have proved particularly suitable, as have aliphatic, aromatic and heterocyclic amines, for example triethylamine, trimethylamine, dimethylaniline, dimethylbenzylamine and pyridine.

Instead of carrying out the reaction in the presence of an acid-binding agent, one may prepare a salt, preferably an alkali metal salt or ammonium salt, of the triazolothiazole derivative (III) in the undiluted form, and then react the salt with the ester halide (II).

The reaction temperature can be varied within a wide range. In general, the reaction is carried out at 0° to 100°C, preferably at 25° to 50°C.

The reaction is in general carried out under normal pressure.

To carry out the process, preferably equimolar amounts of the reactants are combined at the indicated temperatures, optionally in the presence of an acid acceptor and of one of the abovementioned solvents. After stirring the mixture for between one and several hours at elevated temperature, the reaction is complete. Either the reaction mixture is poured into water and extracted by shaking with an organic solvent, for example benzene, and the organic phase is separated off, or it suffices, in some cases, merely to cool the reaction mixture and filter it and then to work up the organic phase in the usual manner by washing, drying and subsequent distillation under reduced pressure. The residue may be subjected to "slight distillation" and at times solidifies to crystals.

Some of the new compounds are obtained in the form of oils which in most cases cannot be distilled without decomposition but can be freed from the last volatile constituents by so-called "slight distillation", that is to say prolonged heating under reduced pressure to moderately elevated temperatures, and they can be purified in this way. They are characterized by their refractive indexes. If the compounds are obtained in crystalline form, they are characterized by their melting points.

As already mentioned, the triazolothiazolyl-(thiono)-phosphoric(phosphonic) acid esters according to the invention are distinguished by an outstanding insecticidal and acaricidal (including tickicidal) action. The new products not only have an action against insects and mites which damage plants but also against hygiene pests and pests of stored products and, in the veterinary medicine field, against ectoparasites, for example parasitic fly larvae and ticks. For this reason, the compounds according to the invention can be employed successfully as pesticides in plant protection and in the hygiene field, the field of protection of stored products and the veterinary field.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft sccale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*); and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado bettle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprises essentially the flies, such as the vingear fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorous moubata*).

When applied against hygiene pests and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates. e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10 percent, preferably 0.01–1 percent, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95 percent, and preferably 0.01–95 percent, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100 percent active substance alone, e.g. about 20–100% by weight of the active compound.

Furthermore, the present invention contemplates methods of selectively killing, combating or controlling pests, e.g. insects and acarids, which comprises applying to at lest one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone
Emulsifier: 1 part by weight of alkylaryl polyglycol ether To produce a suitable preparation of active compound 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100 percent means that all the caterpillars were killed whereas 0 percent means that none of the caterpillars were killed.

The active compounds, the concentrations of the active compounds, the evaluation time and the results can be seen in Table 1.

Table 1

(Plutella test)

| Active compound | Active compound concentration in % by weight | Degree of destruction in % after 3 days |
|---|---|---|
| <br>(known) (A) | 0.1<br>0.01<br>0.001 | 100<br>60<br>0 |
| 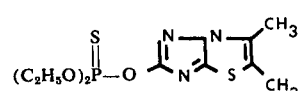<br>(3) | 0.1<br>0.01<br>0.001 | 100<br>100<br>70 |
| 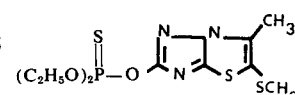<br>(4) | 0.1<br>0.01<br>0.001 | 100<br>100<br>100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100 percent means that all the aphids were killed whereas 0 percent means that none of the aphids were killed.

The active compounds, the concentrations of the active compounds, the evaluation time and the results can be seen in Table 2.

Table 2

(Myzus test)

| Active compound | Active compound concentration in % by weight | Degree of destruction in % after 1 day |
|---|---|---|
| 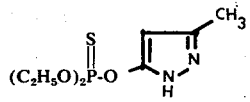 (known) (A) | 0.1<br>0.01<br>0.001 | 99<br>40<br>0 |
| 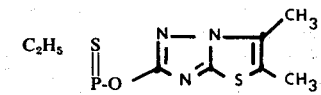 (1) | 0.1<br>0.01<br>0.001 | 100<br>100<br>99 |
| 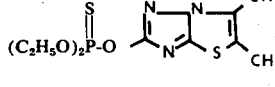 (3) | 0.1<br>0.01<br>0.001 | 100<br>100<br>100 |
| 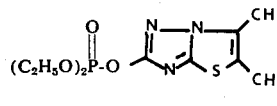 (2) | 0.1<br>0.01<br>0.001 | 100<br>100<br>80 |
| 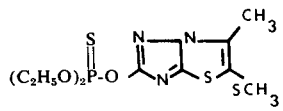 (4) | 0.1<br>0.01<br>0.001 | 100<br>100<br>100 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100 percent means that all the spider mites were killed whereas 0 percent means that none of the spider mites were killed.

The active compound, the concentrations of the active compound, the evaluation time and the results can be seen in Table 3.

Table 3

(Tetranychus test/resistant)
Mites which damage plants

| Active compound | Active compound concentration in % by weight | Degree of destruction in % after 2 days |
|---|---|---|
| 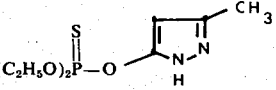 (known) (3) | 0.1<br>0.01 | 50<br>0 |
| 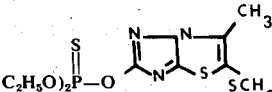 (4) | 0.1<br>0.01 | 100<br>98 |

EXAMPLE 4

LD$_{100}$ test

Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in percent, was determined.

The active compounds, the concentrations of the active compounds, the test insects and the results can be seen in Table 4.

Table 4

(LD$_{100}$ test/*Sitophilus granarius*)

| Active compound | Active compound concentration of the solution in % by weight | Degree of destruction in % |
| --- | --- | --- |
| 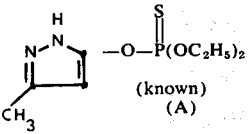 (known) (A) | 0.2<br>0.02 | 100<br>0 |
| 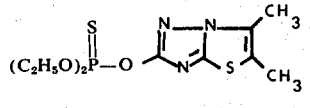 (3) | 0.2<br>0.02 | 100<br>100 |
| 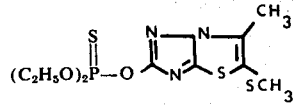 (4) | 0.2<br>0.02<br>0.002 | 100<br>100<br>100 |
| 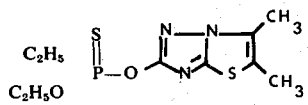 (1) | 0.2<br>0.02 | 100<br>100 |
| 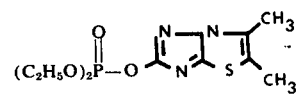 (2) | 0.2<br>0.02 | 100<br>100 |

EXAMPLE 5

Test with parasitic fly larvae

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in percent was determined. 100 percent means that all larvae were killed and 0 percent means no larvae were killed.

The results obtained can be seen in Table 5.

Table 5

(Test with parasitic fly larvae/*Lucilia cuprina*)

| Active compound | Active compound concentration in ppm by weight | Degree of destruction in % |
|---|---|---|
| (4) | 100 | 100 |
|  | 10 | 100 |
|  | 1 | 100 |
| (1) | 100 | 100 |
|  | 10 | 100 |
|  | 1 | 50 |
| (3) | 100 | 100 |
|  | 10 | 100 |
|  | 1 | 100 |
| (2) | 100 | 100 |
|  | 10 | 100 |
|  | 1 | 100 |

EXAMPLE 6

Tick test

Solvent: 35 parts by weight of ethylene glycol monomethyl ether

Emulsifier: 35 parts by weight of nonylphenol polyglycol ether

To prepare a suitable formulation, 3 parts by weight of active compound were mixed with 7 parts of the abovementioned solvent/emulsifier mixture and the emulsion concentrate thus obtained was diluted with water to the particular concentration desired.

Adult fully bloated female ticks of the species *Boophilus microplus* (sensitive or resistant) were dipped into these active compound preparations for one minute. After dipping 10 female specimens of the various species of ticks, the specimens were transferred into Petri dishes, the bottom of which was covered with a filter disc of appropriate size.

After 10 days, the activity of the active compound preparation was assessed by determining the inhibition of deposition of eggs compared to untreated control ticks. The action is expressed in per cent, with 100 percent denoting that eggs were no longer being laid and 0 percent denoting that the ticks laid eggs in normal amount.

The active compound investigated, the concentration tested, the parasites tested and the results obtained can be seen in Table 6.

Table 6

| Active compound | (Tick test/*Boophilus microplus*) Active compound concentration in ppm by weight | Inhibition of deposition of eggs in % (*Boophilus microplus*, Biarra strain) |
| --- | --- | --- |
| (C₂H₅O)₂P(=S)—O—[imidazo-thiazole with CH₃, SCH₃] (4) | 10,000<br>1,000<br>100 | 100<br>100<br>100 |
| C₂H₅(C₂H₅O)P(=S)—O—[imidazo-thiazole with CH₃, CH₃] (1) | 10,000<br>1,000<br>100 | 100<br>100<br>100 |
| (C₂H₅O)₂P(=S)—O—[imidazo-thiazole with CH₃, CH₃] (3) | 10,000<br>1,000<br>100 | 100<br>100<br>100 |
| (C₂H₅O)₂P(=O)—O—[imidazo-thiazole with CH₃, CH₃] (2) | 10,000<br>1,000<br>100 | 100<br>100<br>100 |

EXAMPLE 7

(a)    H₂N—CS—NH—NH—CO—OC₂H₅       (IV)

A mixture of 162 g of pyrocarbonic acid diethyl ester, 91 g of thiosemicarbazide and 300 ml of chloroform was boiled for 3 hours under reflux. After cooling the batch, the precipitate which had separated out was filtered off and recrystallized from ethanol. 121 g (74 percent of theory) of the product of the above formula, of decomposition point 165° to 168°C, were obtained.

(b)

(V)

0.5 mole of sodium methylate was added to 82 g (0.5 mole) of the product prepared as described under (a), in 300 ml of methanol. After heating for 5 hours under reflux, the mixture was cooled and evaporated, the residue was taken up in water and hydrochloric acid was added to the reaction mixture. The precipitate which had separated out was filtered off and dried on clay. 24 g (41 percent of theory) of the above product, of melting point 193°C (with decomposition) were obtained.

(c)

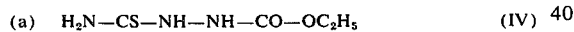

(VI)

107 g of 2-chlorobutanone-(3) were added to 140 g (1 mole) of the sodium salt of the product prepared as described under (b), in 400 ml of ethanol, at 30° to 50°C. The reaction mixture was stirred overnight. It was then poured into 1,000 ml of water and the precipitate which had separated out was filtered off and dried on clay. 78 g (42 percent of theory) of the above product, of melting point 153°C, were obtained.

(d)

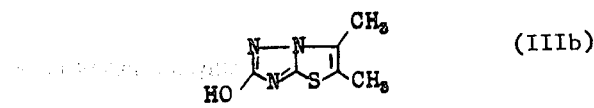

(IIIb)

75 g (0.4 mole) of the product prepared as described under (c) were introduced, in portions, into 140 ml of pure concentrated sulfuric acid, in the course of which the reaction temperature rose to 80°C. The batch was stirred until the solid had dissolved and the reaction solution was then left to stand overnight, poured onto ice and buffered with sodium acetate. The precipitate was filtered off and dried on clay. 27 g (40 percent of theory) of 2,3-dimethyl-6-hydroxy-1,2,4-triazole-(2,3-b)-thiazole of melting point 218° to 220°C were obtained.

(e)

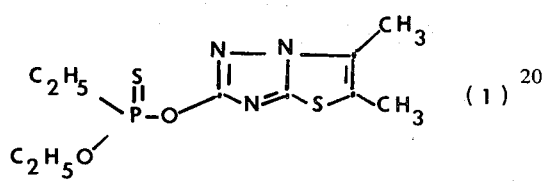  (1)

18 g (0.1 mole) of O-ethyl-thionoethanephosphonic acid ester chloride were added to a mixture of 17 g (0.1 mole) of 2,3-dimethyl-6-hydroxy-1,2,4-triazolo-(2,3-b)-thiazole of (d) and 15 g of potassium carbonate in 200 ml of acetonitrile and the mixture was warmed to 40°C for 4 hours while stirring, then poured into water and extracted by shaking with benzene; after separating the layers, the organic phase was washed and dried and the solvent was distilled off under reduced pressure. The residue solidified to a crystalline mass which was recrystallized from glacial acetic acid/ligroin. 14 g (46 percent of theory) of O-ethyl-O-[2,3-dimethyl-1,2,4-triazolo-(2,3-b)-thiazol(6)-yl]-thionoethanephosphonic acid ester of melting point 76°C were obtained.

EXAMPLE 8

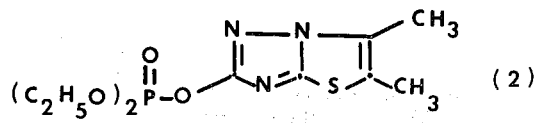  (2)

18 g (0.1 mole) of O,O-diethylphosphoric acid diester chloride were added to a mixture of 21 g (0.1 mole) of 2,3-dimethyl-6-hydroxy-1,2,4-triazolo-(2,3-b)-thiazole produced in Example 7 (d), 15 g of potassium carbonate and 200 ml of acetonitrile, the mixture was warmed to 40°C for 4 hours while stirring and then cooled and freed from the solid constituents, and the solvent was evaporated off under reduced pressure. The residue solidified to a crystalline mass and was recrystallized from glacial acetic acid/ligroin. 19 g (62 percent of theory) of O,O-diethyl-O-[2,3-dimethyl-1,2,4-triazolo-(2,3-b)-thiazol(6)-yl]-phosphoric acid ester of melting point 52°C were obtained.

In analogous manner there was prepared in 56 percent yield

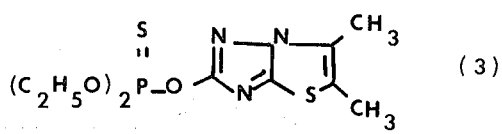  (3)

melting at 79°C.

EXAMPLE 9

(a)

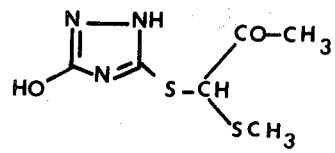

139 g of 1-chloro-1-methylmercaptoacetone (boiling point 65°C/12 mm Hg) were added to 140 g (1 mole) of the sodium salt of the product prepared as described in Example 7 (b) in 500 ml of methanol, and the temperature of the mixture was kept at 0° to 10°C by external cooling. The reaction solution was then left to stand overnight while stirring, the solvent was distilled off under reduced pressure and the residue was triturated with water and then dried on clay. 179 g (82 percent of theory) of the desired product, of melting point 82°C, were thus obtained.

(b)

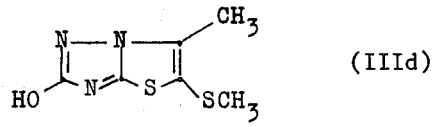  (IIId)

Hydrogen chloride was passed into a solution of 22 g (0.1 mole) of the product prepared as described under (e), in 200 ml of methanol, for 3 hours and at the same time the temperature of the reaction solution was kept at 60° to 65°C. The mixture was then cooled and filtered, the residue was dissolved in water, the aqueous solution was buffered with sodium acetate and the precipitate was filtered off, dried and recrystallized from acetonitrile. 10 g (50 percent of theory) of 2-methylmercapto-3-methyl-6-hydroxy-1,2,4-triazolo-(2,3-b)-thiazole of melting point 138°C were obtained.

(c) By the process of Example 8 the product of (b) was used to synthesize the following compounds:

| Structure | Physical data (refractive index, melting point °C) | Yield (% of theory) |
|---|---|---|
| (4) | $n_D^{23}$: 1.5680 | 79 |
| (5) | 83 | 55 |
| (6) | $n_D^{22}$: 1.5543 | 38 |

It will be appreciated that the instant specification and examples are set forth by way of illustration and not limitation, and that various modifications and changes may be made without departing from the spirit and scope of the present invention.

What is claimed is:

1. An O-alkyl-O-[3-methyl-1,2,4-triazolo-(2,3-b)-thiazol(6)-yl]-(thiono)-phosphoric(phosphoric) acid ester of the formula in which
R is alkyl with 1 to 6 carbon atoms,
R' is alkyl with 1 to 4 carbon atoms, alkoxy with 1 to 6 carbon atoms or phenyl,
R'' is alkyl with 1 to 3 carbon atoms or alkylmercapto with 1 to 3 carbon atoms, and
X is oxygen or sulfur.

2. A compound according to claim 1 in which R has 1 to 3 carbon atoms, R' is alkyl or alkoxy with 1 to 3 carbon atoms or phenyl, and R'' is methyl, ethyl, methylmercapto or ethylmercapto.

3. The compound according to claim 1 wherein such compound is O-ethyl-O-[2,3-dimethyl-1,2,4-triazolo-(2,3-b)-thiazol(6)-yl]-ethanethionophosphonic acid ester of the formula

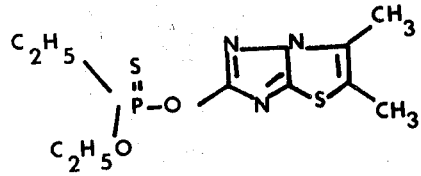

4. The compound according to claim 1 wherein such compound is O,O-diethyl-O-[2,3-dimethyl-1,2,4-triazolo-(2,3-b)-thiazol(6)-yl]-phosphoric acid ester of the formula

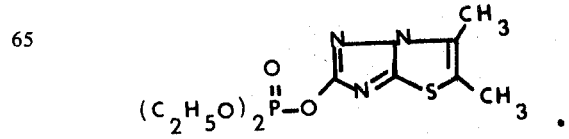

5. The compound according to claim 1 wherein such compound is O,O-diethyl-O-[2,3-dimethyl-1,2,4-triazolo-(2,3-b)-thiazol(6)-yl]-thionophosphoric acid ester of the formula

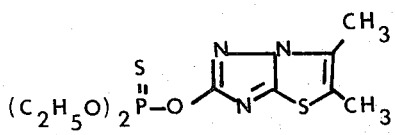

6. The compound according to claim 1 wherein such compound is O,O-diethyl-O-[2-methylmercapto-3-methyl-1,2,4-triazolo-(2,3-b)-thiazol(6)-yl]-thionophosphoric acid ester of the formula

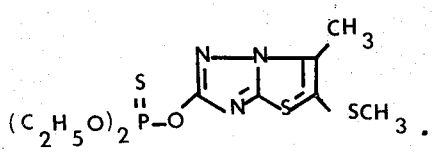

7. The compound according to claim 1 wherein such compound is O,O-dimethyl-O-[2-methylmercapto-3-methyl-1,2,4-triazolo-(2,3-b)-thiazol(6)-yl]-thionophosphoric acid ester of the formula

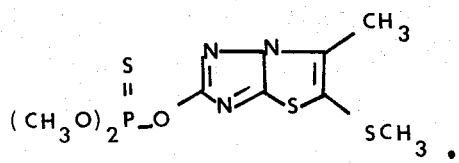

8. The compound according to claim 1 wherein such compound is O-ethyl-O-n-propyl-O-[2-methylmercapto-3-methyl-1,2,4-triazolo-(2,3-b)-thiazol(6)-yl]-thiono-phosphoric acid ester of the formula

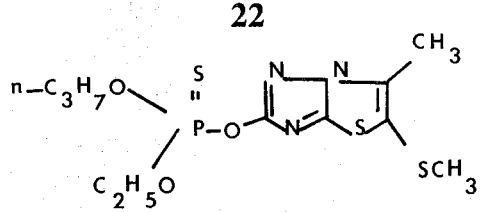

9. An insecticidal or acaricidal composition containing as active ingredient an insecticidally or acaricidally effective amount of a compound according to claim 1 in admixture with a diluent.

10. A method of combating insect or acarid pests which comprises applying to the pests or a habitat thereof an insecticidally or acaricidally effective amount of a compound according to claim 1.

11. The method according to claim 10 in which said pest is an animal ectoparasite.

12. The method according to claim 10 in which the active compound is
   O-ethyl-O-[2,3-dimethyl-1,2,4-triazolo-(2,3-b)-thiazol(6)-yl]-ethanethionophosphonic acid ester,
   O,O-diethyl-O-[2,3-dimethyl-1,2,4-triazolo-(2,3-b)-thiazol(6)-yl]-phosphoric acid ester,
   O,O-diethyl-O-[2,3-dimethyl-1,2,4-triazolo-(2,3-b)-thiazol(6)-yl]-thionophosphoric acid ester,
   O,O-diethyl-O-[2-methylmercapto-3-methyl-1,2,4-triazolo-(2,3-b)-thiazol(6)-yl]-thiono-phosphoric acid ester,
   O,O-dimethyl-O-[2-methylmercapto-3-methyl-1,2,4-triazolo-(2,3-b)-triazol(6)-yl]-thionophosphoric acid ester, or
   O-ethyl-O-n-propyl-O-[2-methylmercapto-3-methyl-1,2,4-triazolo-(2,3-b)-thiazol(6)-yl]-thionophosphoric acid ester.

* * * * *